United States Patent [19]

Moretz et al.

[11] Patent Number: 5,471,683
[45] Date of Patent: Dec. 5, 1995

[54] MOISTURE MANAGEMENT HAT

[75] Inventors: Herbert L. Moretz, Davidson, N.C.; Daniel L. Brier, Key Largo, Fla.

[73] Assignee: Intelpro Corporation, Lincolnton, N.C.

[21] Appl. No.: 118,032

[22] Filed: Sep. 8, 1993

Related U.S. Application Data

[63] Continuation-in-part of Ser. No. 2,650, Jan. 11, 1993, Pat. No. 5,306,536.

[51] Int. Cl.$^6$ .................................................... A42B 1/00
[52] U.S. Cl. ........................... 2/181; 2/DIG. 11; 2/169; 2/170
[58] Field of Search ...................... 2/181, 171, DIG. 11; 66/169 R, 170, 171, 185; 428/93

[56] References Cited

U.S. PATENT DOCUMENTS

| | | |
|---|---|---|
| 2,166,012 | 7/1939 | La Maida . |
| 2,495,863 | 1/1950 | Paige . |
| 2,629,380 | 2/1953 | Schweikert . |
| 2,828,745 | 4/1958 | Deutz . |
| 3,237,625 | 3/1966 | Johnson . |
| 3,508,550 | 4/1970 | Vollrath . |
| 3,613,687 | 10/1971 | Kennedy . |
| 3,714,946 | 2/1973 | Rudes . |
| 4,338,371 | 7/1982 | Dann et al. ............................ 428/283 |
| 4,341,096 | 7/1982 | Safrit et al. .............................. 66/185 |
| 4,502,156 | 3/1985 | Wishman ................................... 2/181 |
| 4,675,915 | 6/1987 | Siciliano .................................... 2/181 |
| 4,844,965 | 7/1989 | Foxman . |
| 4,856,116 | 8/1989 | Sullivan ..................................... 2/181 |
| 4,961,982 | 10/1990 | Taylor . |
| 4,981,738 | 1/1991 | Farnworth et al. . |
| 5,021,280 | 6/1991 | Farnworth et al. . |
| 5,037,409 | 8/1991 | Chen et al. . |
| 5,105,476 | 4/1992 | Cox ................................... 2/DIG. 11 |
| 5,181,277 | 1/1993 | Sherman .................................... 2/181 |
| 5,217,782 | 6/1993 | Moretz et al. ............................ 428/91 |

OTHER PUBLICATIONS

The Sign of Winners, by Akzo Fibres, undated.
Hydrofil nylon, by Allied Signal Inc., 1988.
Industrial Fabric Opportunites for Hydrophilic Nylons, by Judy Peters, 1990.

*Primary Examiner*—Clifford D. Crowder
*Assistant Examiner*—Gloria Hale
*Attorney, Agent, or Firm*—W. Thad Adams, III

[57] ABSTRACT

A moisture management hat is constructed of a shell fabric and includes a moisture management band. The moisture management band is located along an inside perimeter of the hat for residing next to at least the forehead of the wearer during garment wear. The moisture management band includes a first, moisture wicking fabric layer having a skin-side surface and a shell-side surface. The first fabric layer is constructed of hydrophobic fibers for residing nearest the head of the wearer for moving moisture outwardly away from the head. A second, moisture dispersal fabric layer having a skin-side surface and a shell-side surface resides adjacent to the shell-side surface of the first fabric layer. The second fabric layer is constructed of hydrophilic fibers for receiving and dispersing moisture wicked outwardly by the first fabric layer.

12 Claims, 9 Drawing Sheets

MOISTURE MANAGEMENT HAT

TECHNICAL FIELD AND BACKGROUND OF THE INVENTION

This application is a continuation-in-part application of U.S. Ser. No. 002,650, U.S. Pat. No. 5,306,536. The invention relates to a moisture management system for hats. The invention is applicable to hats of all styles and designs, and is especially suited for hats worn primarily outdoors where the wearer is more likely to perspire.

Heavy perspiration on the brow and forehead often results from physical activity in a warm environment. During such activity, particularly outdoors, many people choose to wear a hat. For those people with a receding hairline or baldness, the need for a good, comfortable hat is all but essential for obtaining suitable relief from the heat, and sun exposure to the head. Moreover, as the awareness and concern of skin cancer steadily increases, people will further appreciate the benefit of wearing proper headgear during outdoor activities. Thus, there exists a need for an improved hat which effectively handles moisture from the head of the wearer, and draws the moisture outwardly away from the head to a drier area of the hat for evaporation.

Conventional hat designs are inadequate for managing perspiration. Typically, as the wearer begins to perspire, moisture is absorbed directly into the outer shell fabric of the hat or into the bill of the hat where it remains for several hours during and after wear. This is not only uncomfortable to the wearer, but can also damage and stain the hat.

The present invention addresses the need for a hat which effectively handles head perspiration moisture by moving the moisture to areas of the hat where it can be more readily evaporated. The hat of this invention is more resistant to damage and stains caused by moisture perspiration, and thus provides to the wearer a more attractive and comfortable hat.

SUMMARY OF THE INVENTION

Therefore, it is an object of the invention to provide a moisture management hat which effectively handles head perspiration moisture by moving the moisture outwardly away from the head and upwardly to drier areas of the hat for evaporation.

It is another object of the invention to provide a moisture management hat which resists damage and stains caused by heavy perspiration moisture.

It is another object of the invention to provide a moisture management system which can be incorporated into any style of hat, such as baseball caps, golf hats, brimmed dress hats for men and women, western style hats, safari style hats, and other various styles.

It is another object of the invention to provide a moisture management hat which includes a moisture management band located along an inside perimeter of the hat for quickly moving moisture away from the head of the wearer.

It is another object of the invention to provide a moisture management hat which further includes a moisture transport insert located at an inside front crown portion of the hat for further moving moisture outwardly away from the head of the wearer and upwardly to drier areas of the hat for evaporation.

It is another object of the invention to provide a moisture management hat constructed of an outer shell fabric including at least one moisture evaporation panel positioned adjacent to the moisture transport insert and the moisture management band for further enhancing the evaporation of moisture from the hat.

These and other objects of the present invention are achieved in the preferred embodiments disclosed below by providing a moisture management hat constructed of a shell fabric and including a moisture management band. The moisture management band is located along an inside perimeter of the hat for residing next to at least the forehead of the wearer during garment wear. The moisture management band includes a first, moisture wicking fabric layer having a skin-side surface and a shell-side surface. The first fabric layer is constructed of hydrophobic fibers for residing nearest the head of the wearer for moving moisture outwardly away from the head.

The moisture management band further includes a second, moisture dispersal fabric layer having a skin-side surface and a shell-side surface. The second fabric layer resides adjacent to the shell-side surface of the first fabric layer, and is constructed of hydrophilic fibers for receiving and dispersing moisture wicked outwardly by the first fabric layer.

According to one preferred embodiment of the invention, the first and second fabric layers are integrally knit.

Preferably, the skin side surface of the first fabric layer is brushed to raise the hydrophobic fibers and enhance the outward movement of moisture along the fibers.

According to another preferred embodiment of the invention, the moisture management band includes a third fabric layer having a skin-side surface and a shell-side surface. The third fabric layer is integrally knit with the first and second fabric layers, and resides substantially adjacent to the shell-side surface of the second fabric layer. The third fabric layer is constructed of hydrophilic fibers for further receiving and dispersing moisture moved outwardly by the first and second fabric layers.

Preferably, the shell-side surface of the third fabric layer is brushed to increase the quantity of hydrophilic fiber ends extending from the moisture management band, thereby increasing the fabric surface area available for air exposure and enhancing the evaporation of moisture from the moisture management band.

According to another preferred embodiment of the invention, the shell fabric of the hat includes a first moisture evaporation panel located on a front crown portion of the hat. The first evaporation panel is constructed of an air permeable, relatively open knit or woven fabric.

According to yet another preferred embodiment of the invention, the shell fabric of the hat further includes a second moisture evaporation panel located along the perimeter of the hat generally adjacent to the moisture management band. The second moisture evaporation panel is constructed of an air permeable, relatively open knit or woven fabric.

According to one preferred embodiment of the invention, a moisture management hat constructed of a shell fabric includes a moisture management band and a moisture transport insert. The moisture management band is located along an inside perimeter of the hat for residing next to at least the forehead of the wearer during garment wear. The moisture management band includes a first, moisture wicking fabric layer having a skin-side surface and a shell-side surface. The first fabric layer is constructed of hydrophobic fibers for moving moisture outwardly away from the head of the wearer. A second, moisture dispersal fabric layer having a skin-side surface and a shell-side surface resides adjacent to the shell-side surface of the first fabric layer. The second fabric layer is constructed of hydrophilic fibers for receiving and dispersing moisture wicked outwardly by the first fabric layer.

The moisture transport insert is located generally at an inside front crown portion of the hat. The moisture transport insert has a lower section which resides adjacent to the shell-side surface of the second fabric layer of the moisture management band. The moisture transport insert includes a first fabric layer having a skin-side surface and a shell-side surface. The first fabric layer is constructed of hydrophobic wicking fibers for moving moisture outwardly and upwardly away from the forehead of the wearer.

According to another preferred embodiment of the invention, the moisture transport insert further includes a second fabric layer having a skin-side surface and a shell-side surface. The second fabric layer is integrally knit with the first fabric layer of the moisture transport insert, and resides adjacent to the shell-side surface of the first fabric layer. The second fabric layer is constructed of hydrophilic fibers for moving moisture outwardly away from the forehead and upwardly towards the front crown portion of the hat for dispersal and evaporation.

According to yet another preferred embodiment of the invention, the moisture transport insert further includes a third fabric layer having a skin-side surface and a shell-side surface. The third fabric layer is integrally knit with the first and second fabric layers of the moisture transport insert, and resides adjacent to the shell-side surface of the second fabric layer. The third fabric layer is constructed of hydrophilic fibers for moving moisture outwardly away from the forehead and upwardly towards the front crown portion of the hat for dispersal and evaporation.

Preferably, the shell-side surface of the third fabric layer is brushed to increase the quantity of hydrophilic fiber ends extending from the moisture transport insert, thereby increasing the fabric surface area available for air exposure and enhancing the evaporation of moisture from the moisture transport insert.

According to another preferred embodiment of the invention, the shell fabric of the hat includes a first moisture evaporation panel located on a front crown portion of the hat. The first evaporation panel is constructed of an air permeable, relatively open knit or woven fabric.

According to another preferred embodiment of the invention, the shell fabric of the hat further includes a second moisture evaporation panel located along the perimeter of the hat generally adjacent to the moisture management band. The second moisture evaporation panel is constructed of an air permeable, relatively open knit or woven fabric.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
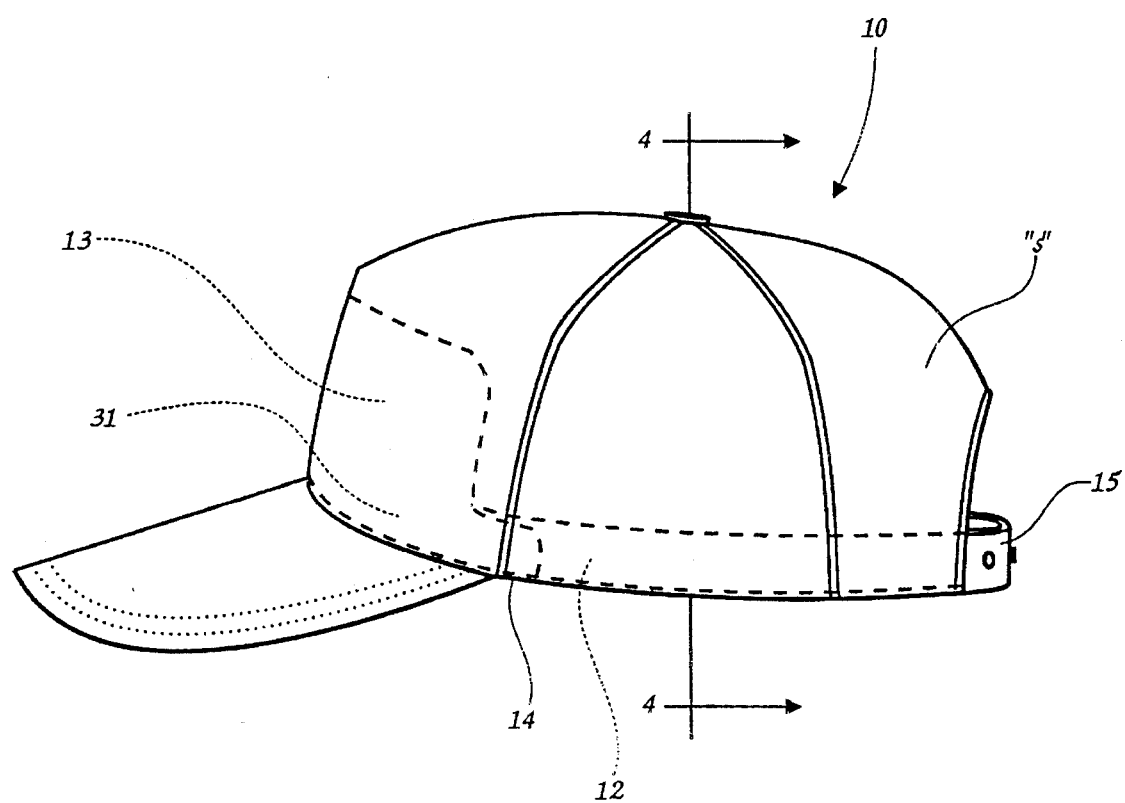
FIG. 1 is a side view of a hat according to one embodiment of the present invention.

Referring now specifically to the drawings, a moisture management hat according to the present invention is illustrated in FIG. 1 and shown generally at reference numeral 10. The moisture management hat 10 is described below with reference to a conventional-type cap such as worn by baseball players or golfers, as shown in FIG. 1. However, the invention is not limited to such conventional-type caps, but instead includes all hats of various design and appearance, such as brimmed dress hats for men and women, western style hats, and safari style hats. Slight modifications of the shape and placement of the below-described moisture management components may be necessary to accommodate the numerous varieties of hat styles.

Figure 2:
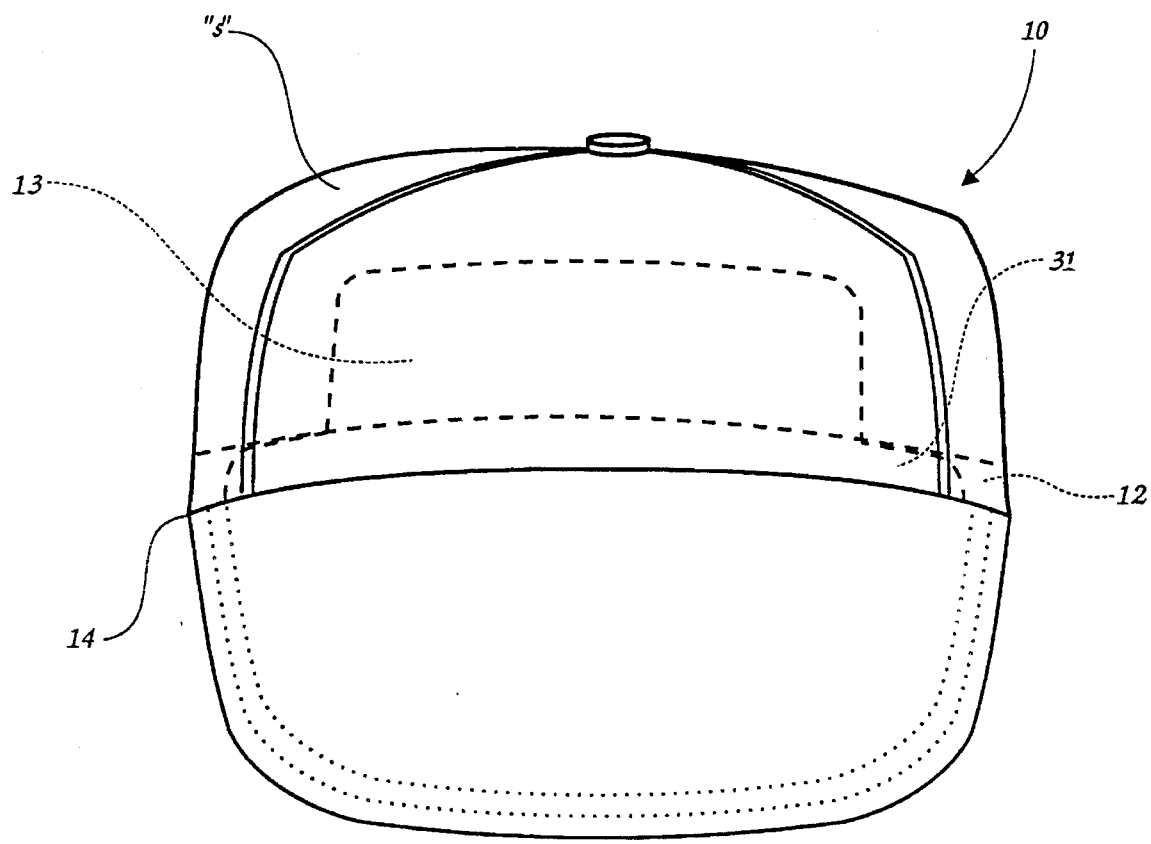
FIG. 2 is a front view of the hat illustrated in FIG. 1.
Figure 3:
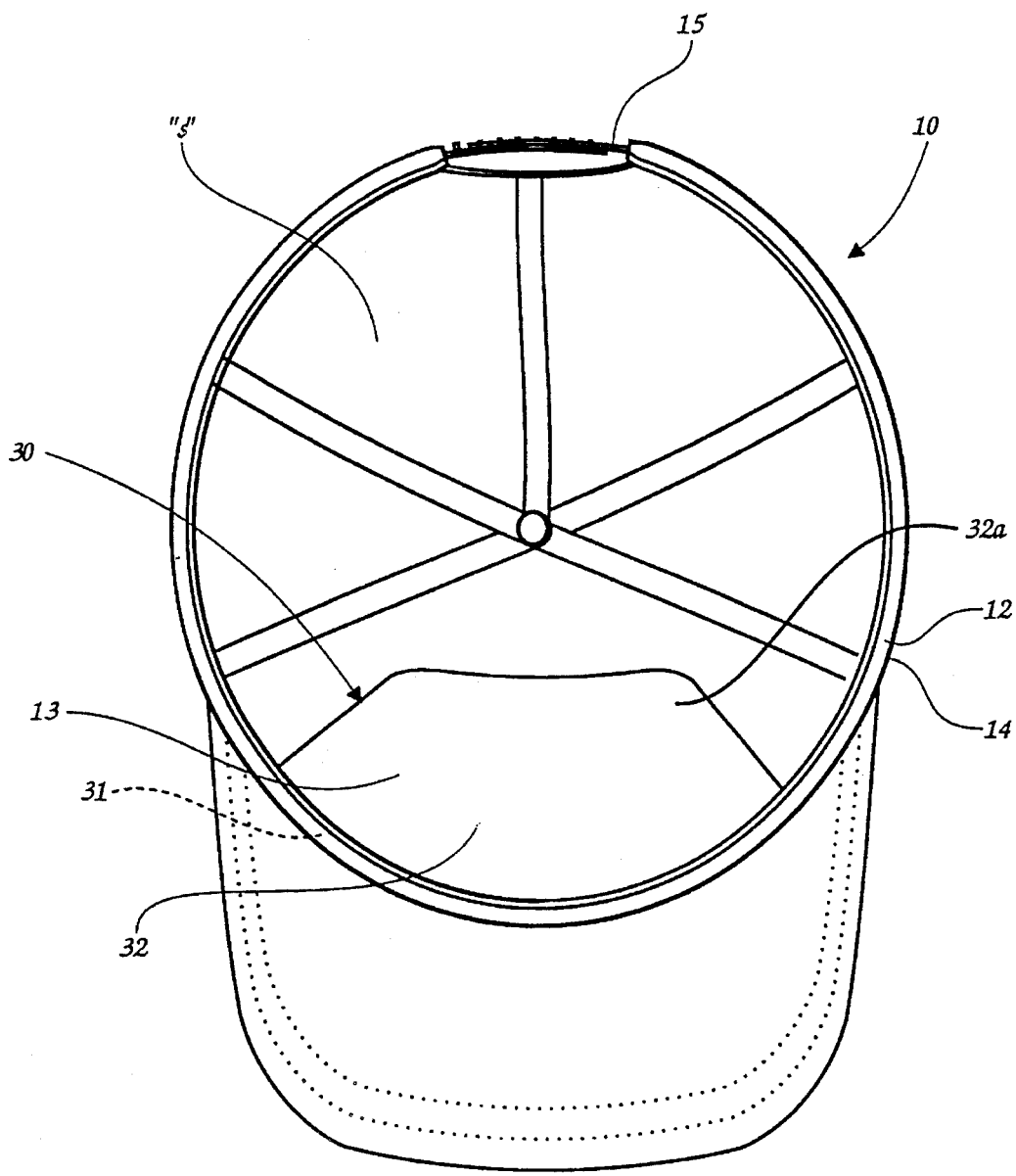
FIG. 3 is an inside view of the hat illustrated in FIGS. 1 and 2.

The moisture management hat 10 is constructed of any suitable knit or woven outer shell fabric "S" such as cotton, or various cotton/polyester or nylon blends. Preferably, the moisture management hat 10 includes both a multi-layer moisture management band 12 and moisture transport insert 13, as shown in FIGS. 1, 2, and 3. However, either component may be included without the other for attaining a lesser degree of moisture management.

Referring to FIGS. 1, 2, and 3, the moisture management band 12 is located along the inside perimeter 14 of the hat 10, and resides next to at least the forehead of the wearer during garment wear. The moisture management band 12 is preferably knit but may be woven, or constructed of bonded non-woven fibers. Preferably, the moisture management band 12 extends along the entire inside perimeter 14 of the hat 10, excluding the adjustment strap 15 located in back perimeter portion of the hat 10 (See FIGS. 1 and 3).

Figure 4:
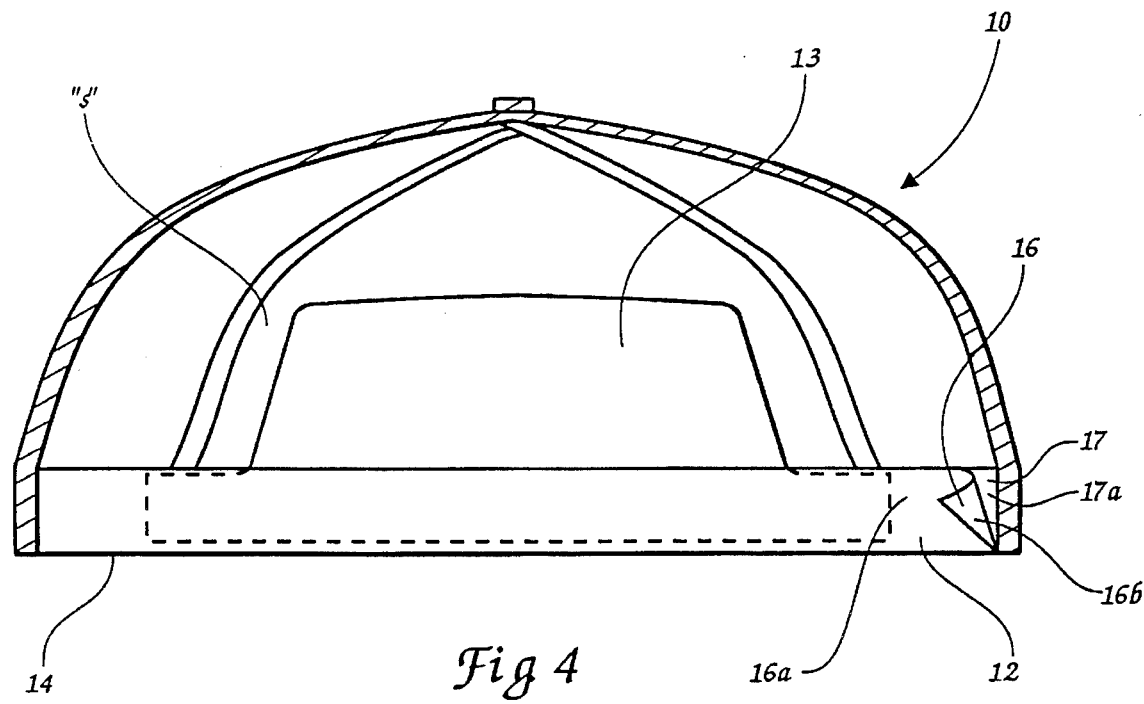
FIG. 4 is a is cross-sectional view taken substantially along line 4—4 of FIG. 1, showing an inside view of the hat from the back side of the hat.
Figure 5:
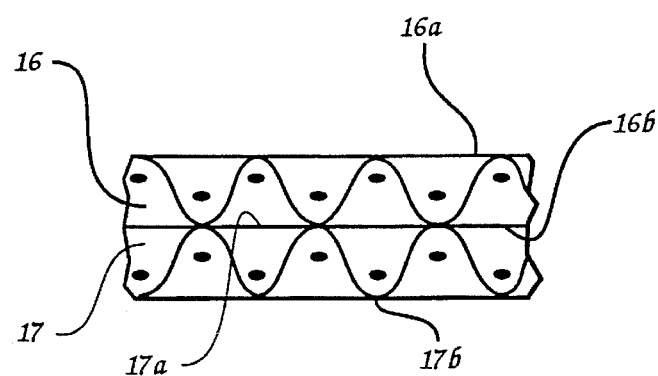
FIG. 5 is a fragmentary, schematic cross-sectional view with thickness exaggerated of the moisture management band shown in FIG. 4.

As shown in FIGS. 4 and 5, the moisture management band 12 includes a first, preferably knit, moisture wicking fabric layer 16 constructed of non-absorbent hydrophobic wicking fibers. The first fabric layer 16 resides nearest the head of the wearer during garment wear. The hydrophobic fibers operate to quickly move moisture outwardly, away from the skin and hair of the wearer. Preferably, the hydrophobic fibers are chosen from the fiber group including polyester, polypropylene, and polyethylene. Alternately, the first fabric layer 16 may be constructed of hydrophobic wicking fibers such as the polyester fibers manufactured by DuPont under the trademark "Coolmax." The "Coolmax" fibers have a relatively large surface area in relation to volume. Additionally, these such fibers provide four channels along their respective longitudinal dimensions to encourage the wicking of moisture, and to facilitate the interface with air.

The first fabric layer 16 of the moisture management band 12 has a skin-side surface 16a and a shell-side surface 16b. These terms indicate the side of the fabric layer closer to the skin during garment wear, and the side closer to the shell fabric of the moisture management hat, respectively. They are not intended to infer that the skin-side surface of the fabric layer must be in direct contact with the skin, or that the shell-side surface must be in direct contact with the shell fabric of the moisture management hat 10.

The skin-side surface 16a of the first fabric layer 16 may be brushed to raise the hydrophobic wicking fibers, thereby creating a napped surface. The brushed or napped surface enhances the outward movement of moisture along the longitudinal shafts of the hydrophobic fibers to more quickly wick moisture from the head.

Preferably, the moisture management band 12 further includes a second moisture dispersal fabric layer 17 having a skin-side surface 17a and a shell-side surface 17b. The second fabric layer 17 resides adjacent to the shell-side surface 16b of the first fabric layer 16 of the moisture management band 12, and is preferably integrally knit to the first fabric layer 16. The second fabric layer 17 is constructed of hydrophilic fibers for receiving and dispersing moisture wicked outwardly by the first fabric layer 16. Thus, as the wearer begins to perspire, moisture is wicked away from the head and pushed by body heat along the hydrophobic fibers of the first fabric layer 16. From the first fabric layer 16, the moisture is further drawn outwardly by the absorbent fibers of the second fabric layer 17 where the moisture is more readily evaporated.

The hydrophilic fibers of the second fabric layer 17 are chosen from the fiber group including hydrophilic nylon, cotton, rayon, wool, or other similar fibers. Preferably, the hydrophilic fibers of the second fabric layer 17 are hydrophilic nylon fibers such as those manufactured by Allied Fibers under the trademark "Hydrofil."

Referring again to FIGS. 1, 2, and 3, the moisture transport insert 13 is located generally at an inside front crown portion 30 (See FIG. 3) of the moisture management hat 10. The moisture transport insert 13 includes a lower section 31 positioned adjacent to the shell-side surface of the moisture management band 12, such that the moisture management band 12 resides in direct contact with the head of the wearer during garment wear. Preferably, the lower section 31 of the moisture transport insert 13 extends generally from one temple of the wearer to the other temple during garment wear.

Figure 3A:
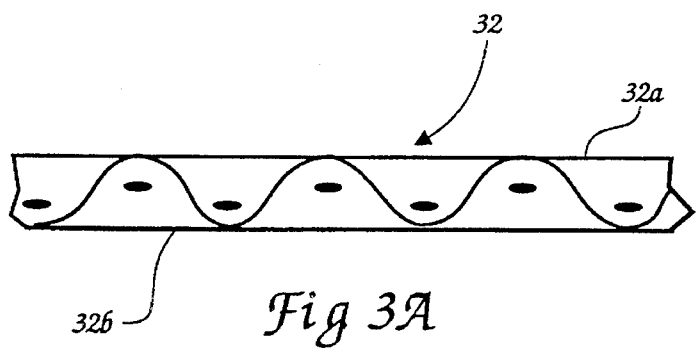
FIG. 3A is an enlarged cross-sectional view showing the fabric layer of the moisture transport insert according to one preferred embodiment of the invention.

The moisture transport insert 13 is preferably knit, and is constructed of a fabric layer 32 (See FIGS. 3 and 3A) having a skin-side surface 32a and a shell-side surface 32b. The first fabric layer 32 includes hydrophobic wicking fibers for moving moisture outwardly and upwardly away from the forehead of the wearer to a drier area of the hat 10 where moisture is more easily evaporated. Preferably, the hydrophobic fibers are polyester fibers produced by DuPont under the trademark "Coolmax." As noted above, these such fibers have a relatively large surface area in relation to volume, and provide four channels along their respective longitudinal dimensions. This encourages wicking of moisture, and facilitates the interface with air.

Figure 6:
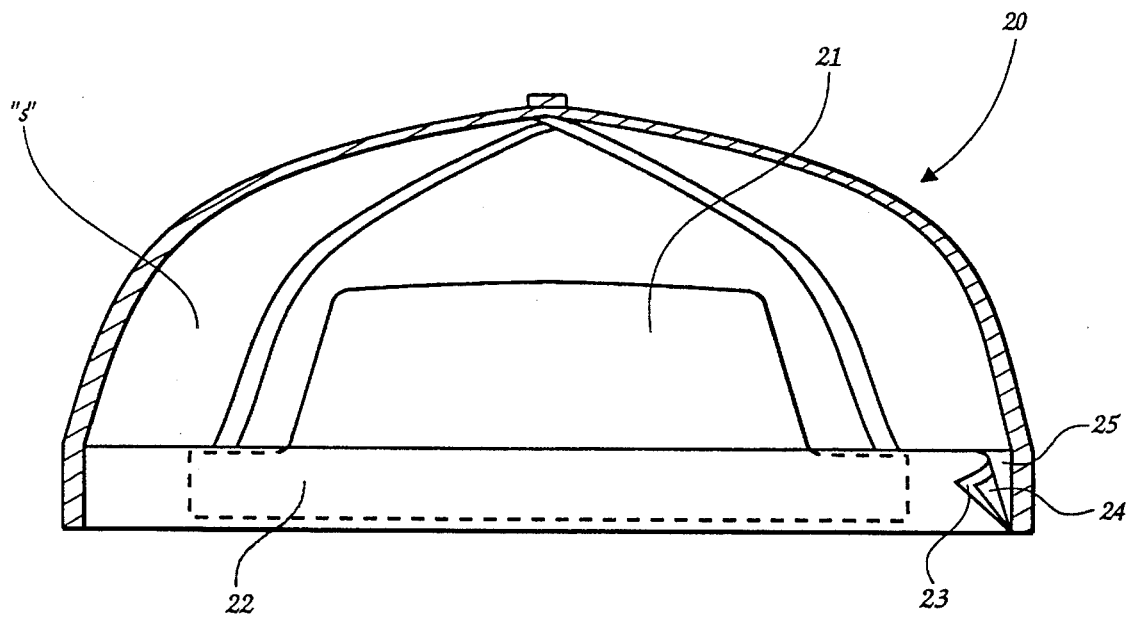
FIG. 6 is a cross-sectional view similar to that shown in FIG. 4 according to another embodiment of the invention illustrating the moisture management band with fabric layers peeled back.
Figure 7:
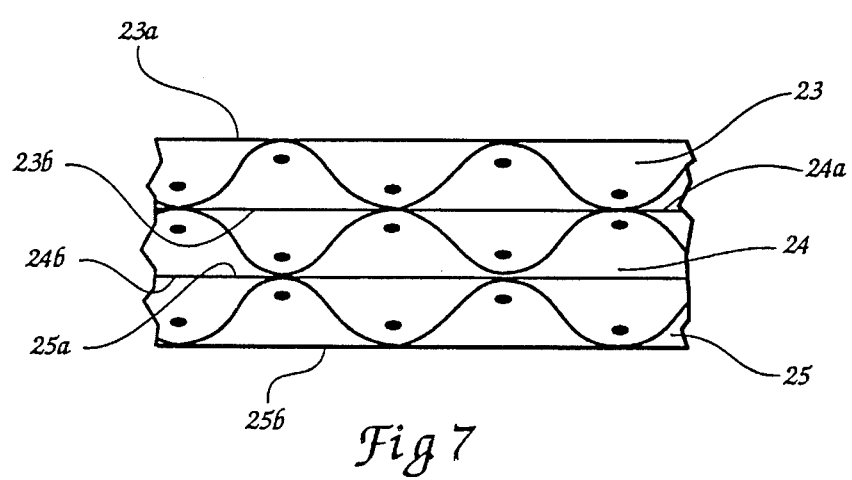
FIG. 7 is a fragmentary, schematic cross-sectional view with thickness exaggerated of the moisture management band shown in FIG. 6.

Referring now to FIGS. 6 and 7, a second embodiment of a moisture management hat 20 including a moisture management band 22 and moisture transport insert 21 is shown. The fabric construction of the moisture transport insert 21 may be identical to that described above. Alternately, the moisture transport insert 21 may be constructed according to any one of the embodiments described in detail below.

As shown in FIGS. 6 and 7, the moisture management band 22 of the moisture management hat 20 includes three fabric layers 23, 24, and 25. Of these three fabric layers, the first fabric layer 23 resides nearest the head of the wearer during garment wear. The first fabric layer 23 has a skin-side surface 23a and a shell-side surface 23b, and is constructed of hydrophobic wicking fibers. The skin-side surface 23a of the first fabric layer 23 may be brushed to raise the hydrophobic wicking fibers, thereby creating a napped surface. The brushed or napped surface enhances the outward movement of moisture along the longitudinal shafts of the hydrophobic fibers to more quickly wick moisture from the head.

The second fabric layer 24 of the moisture management band 22 has a skin-side surface 24a and a shell-side surface 24b. The second fabric layer 24 resides adjacent to the shell-side surface 23b of the first fabric layer 23, and is preferably integrally knit to the first fabric layer 23.

The second fabric layer 24 is constructed of hydrophilic fibers for receiving and dispersing moisture wicked outwardly by the first fabric layer 23. The hydrophilic fibers are chosen from the fiber group including hydrophilic nylon, cotton, rayon, wool, or other similar fibers. Preferably, the hydrophilic fibers of the second fabric layer 24 are hydrophilic nylon fibers such as those manufactured by Allied Fibers under the trademark Hydrophil.

The third fabric layer 25 resides nearest the outer shell "S" of the moisture management hat 20, and has a skin-side surface 25a and a shell-side surface 25b. Preferably, the third fabric layer 25 is integrally knit with the first and second fabric layers 23 and 24, and resides substantially adjacent to the shell-side surface 24b of the second fabric layer 24. The third fabric layer 25 is constructed of hydrophilic fibers which act to further receive and disperse moisture moved outwardly by the first and second fabric layers 23 and 24. The hydrophilic fibers of the third fabric layer 25 are chosen from the fiber group including hydrophilic nylon, cotton, rayon, wool, or other similar fibers.

Preferably, the shell-side surface 25b of the third fabric layer 25 is brushed to create a napped surface. Brushing the shell-side surface 25b greatly increases the quantity of hydrophilic fiber ends that extend outwardly from the moisture management band 22. This increases the surface area available for moisture-air interface which thereby enhances evaporation of moisture from the band 22.

The tri-layer fabric of the moisture management band 22, described above, may be a multi-layer moisture management fabric according to that disclosed in Applicant's pending application U.S. Ser. No. 002,650.

Figure 8:
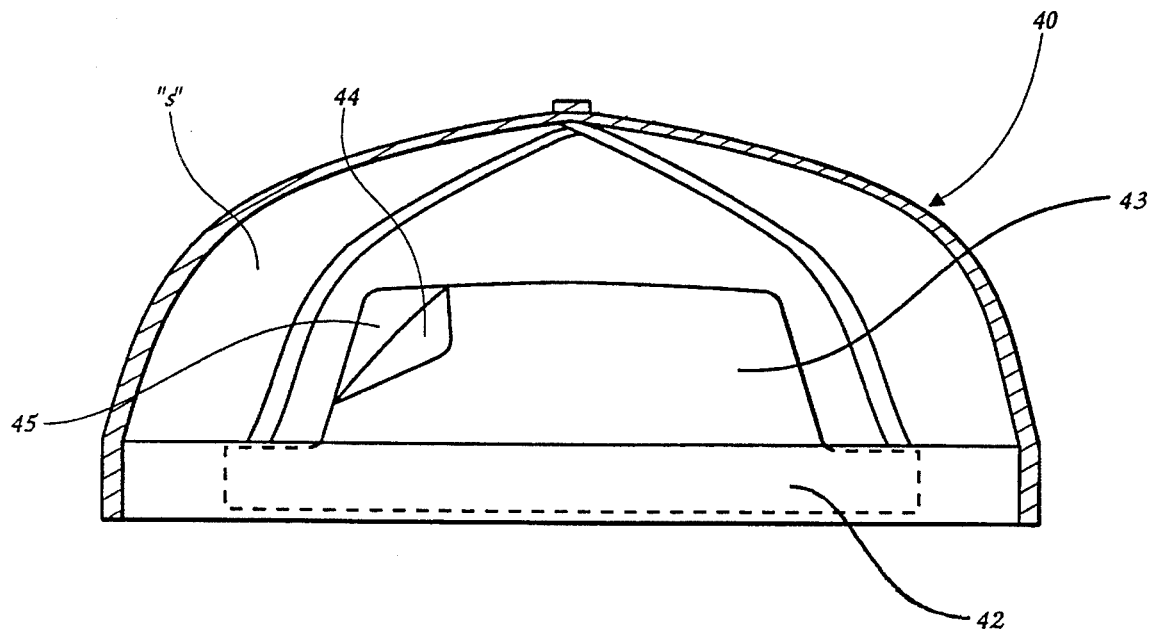
FIG. 8 is a cross-sectional view similar to that shown in FIGS. 4 and 6, according to another embodiment of the invention and illustrating a second embodiment of the moisture transport insert with fabric layers peeled back.
Figure 9:
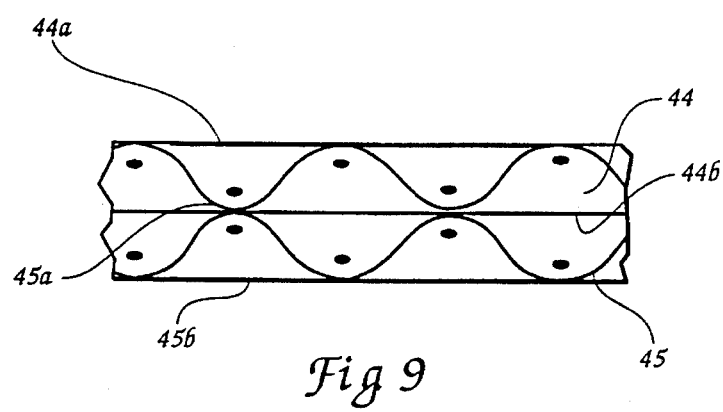
FIG. 9 is a fragmentary, schematic cross-sectional view with thickness exaggerated of the moisture transport insert shown in FIG. 8.

Referring now to FIGS. 8 and 9, a third embodiment of a moisture management hat 40 including a moisture management band 42 and moisture transport insert 43 is shown. The moisture management band 42 may be constructed according to that described above with reference to the moisture management band 12 or 22 of FIGS. 4 and 5, and FIGS. 6 and 7, respectively.

As shown in FIGS. 8 and 9, the moisture transport insert 43 of the moisture management hat 40 includes first and second fabric layers 44 and 45. Of these two fabric layers, the first fabric layer 44 resides nearest the head during garment wear. The first fabric layer 44 is preferably knit, and has a skin-side surface 44a and a shell-side surface 44b. The first fabric layer 44 is constructed of hydrophobic wicking fibers for moving moisture outwardly and upwardly away from the forehead of the wearer to a drier area of the hat 40 where moisture is more easily evaporated. Preferably, the hydrophobic wicking fibers are the polyester fibers produced by DuPont under the trademark "Coolmax." These such fibers have a relatively large surface area in relation to volume, and provide four channels along their respective longitudinal dimensions. This encourages wicking of moisture, and facilitates the interface with air.

The second fabric layer 45 resides nearest the outer shell "S" of the moisture management hat 40. Preferably, the second fabric layer 45 is integrally knit to the first fabric layer 44, and has a skin-side surface 45a and a shell-side surface 45b. The skin-side surface 45a of the second fabric layer 45 resides adjacent to the shell-side surface 44b of the first fabric layer 44. The second fabric layer 45 is constructed of hydrophilic fibers, such as cotton, rayon, or hydrophilic nylon. The second fabric layer 45 acts to receive moisture from the first fabric layer 44 and the moisture management band 42, and to further wick the moisture upwardly away from the brow of the garment wearer. The moisture is subsequently dispersed through the hydrophilic fibers of the second fabric layer 45 and positioned on the shell-side surface 45b of the second fabric layer 45 to facilitate evaporation from the moisture management hat 10.

Figure 10:
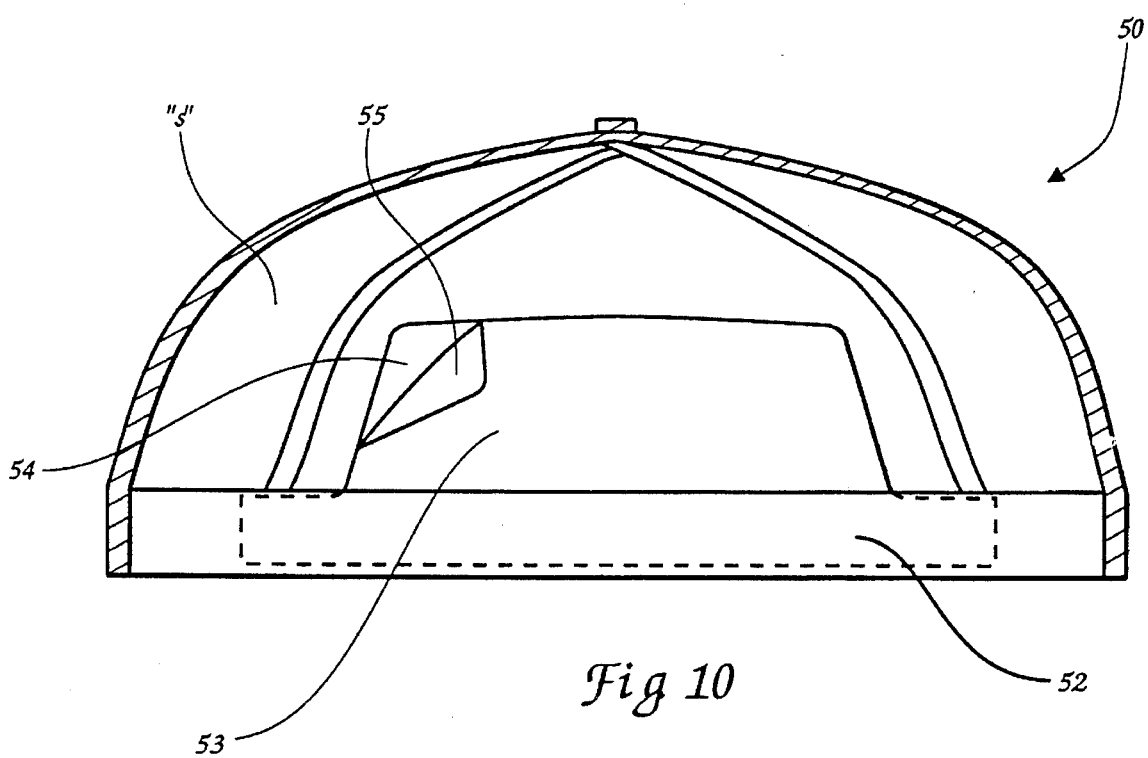
FIG. 10 is a cross-sectional view similar to that shown in FIGS. 4, 6, and 8, according to another embodiment of the invention and illustrating a third embodiment of the moisture transport insert with fabric layers peeled back.
Figure 11:
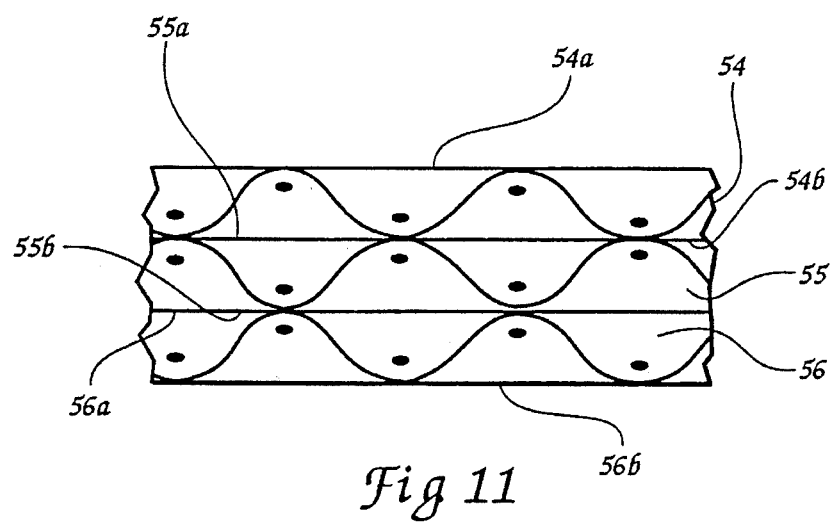
FIG. 11 is a fragmentary, schematic cross-sectional view with thickness exaggerated of the moisture transport insert shown in FIG. 10.

Referring to FIGS. 10 and 11, a fourth embodiment of a moisture management hat 50 including a moisture management band 52 and moisture transport insert 53 is shown. The moisture management band 52 may be constructed according to that described above with reference to the moisture management band 12 or 22 of FIGS. 4 and 5, and FIGS. 6 and 7, respectively.

As shown in FIGS. 10 and 11, the moisture transport insert 53 of the moisture management hat 50 includes three fabric layers 54, 55, and 56. Of these three fabric layers, the first fabric layer 54 resides nearest the head during garment wear. The first fabric layer 54 is preferably knit, and has a skin-side surface 54a and a shell-side surface 54b. The first fabric layer 54 is constructed of hydrophobic wicking fibers for moving moisture outwardly and upwardly away from the forehead of the wearer to a drier area of the hat 50 where moisture is more easily evaporated. Preferably, the hydrophobic fibers are polyester fibers produced by DuPont under the trademark "Coolmax." These such fibers have a relatively large surface area in relation to volume, and provide four channels along their respective longitudinal dimensions. This encourages wicking of moisture, and facilitates the interface with air.

The second fabric layer 55 is integrally knit to the first fabric layer 54, and has a skin-side surface 55a and a shell-side surface 55b. The skin-side surface 55a of the second fabric layer 55 resides adjacent to the shell-side surface 54b of the first fabric layer 54. The second fabric layer 55 includes hydrophilic fibers, such as cotton, rayon, or hydrophilic nylon. The second fabric layer 55 acts to receive moisture from the first fabric layer 54 and the moisture management band 52, and to further wick the moisture upwardly away from the brow of the garment wearer. The moisture is subsequently dispersed through the hydrophilic fibers of the second fabric layer 55 and positioned on the shell-side surface 55b of the second fabric layer 55 to facilitate evaporation from the moisture management hat 50.

The third fabric layer 56 resides nearest the outer shell "S" of the moisture management hat 50. Preferably, the third fabric layer 56 is integrally knit with the first and second fabric layers 54 and 55, and has a skin-side surface 56a and a shell-side surface 56b. The third fabric layer 56 resides substantially adjacent the shell-side surface 55b of the second fabric layer 55. Preferably, the third fabric layer 56 is constructed of hydrophilic fibers, such as hydrophilic nylon fibers. Additionally, the shell-side surface 56b of the third fabric layer 56 may be brushed to increase the interface of fibers and air, thereby enhancing evaporation of moisture from the fibers.

The tri-layer fabric of the moisture management band 22, described above, may be a multi-layer moisture management fabric according to that disclosed in Applicant's pending application U.S. Ser. No. 002,650.

Figure 12:
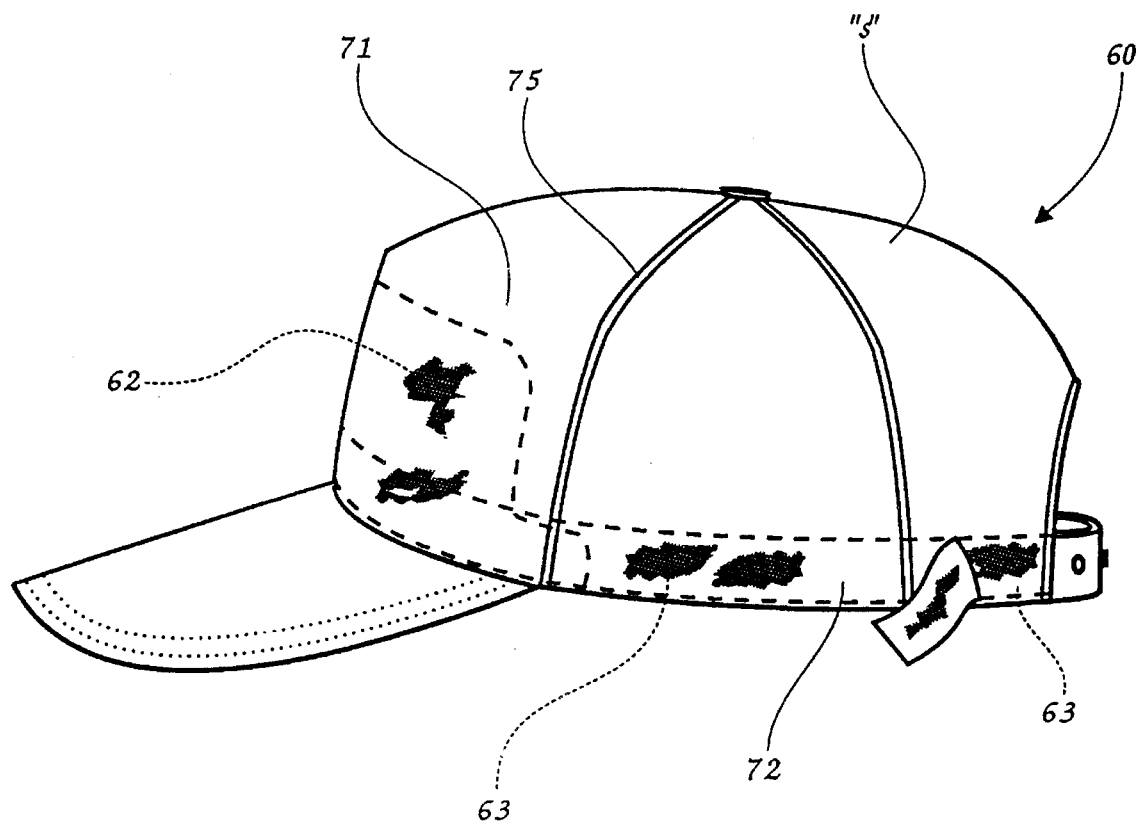
FIG. 12 is a side view of a hat according to another embodiment of the invention showing particularly the moisture evaporation panels.
Figure 13:
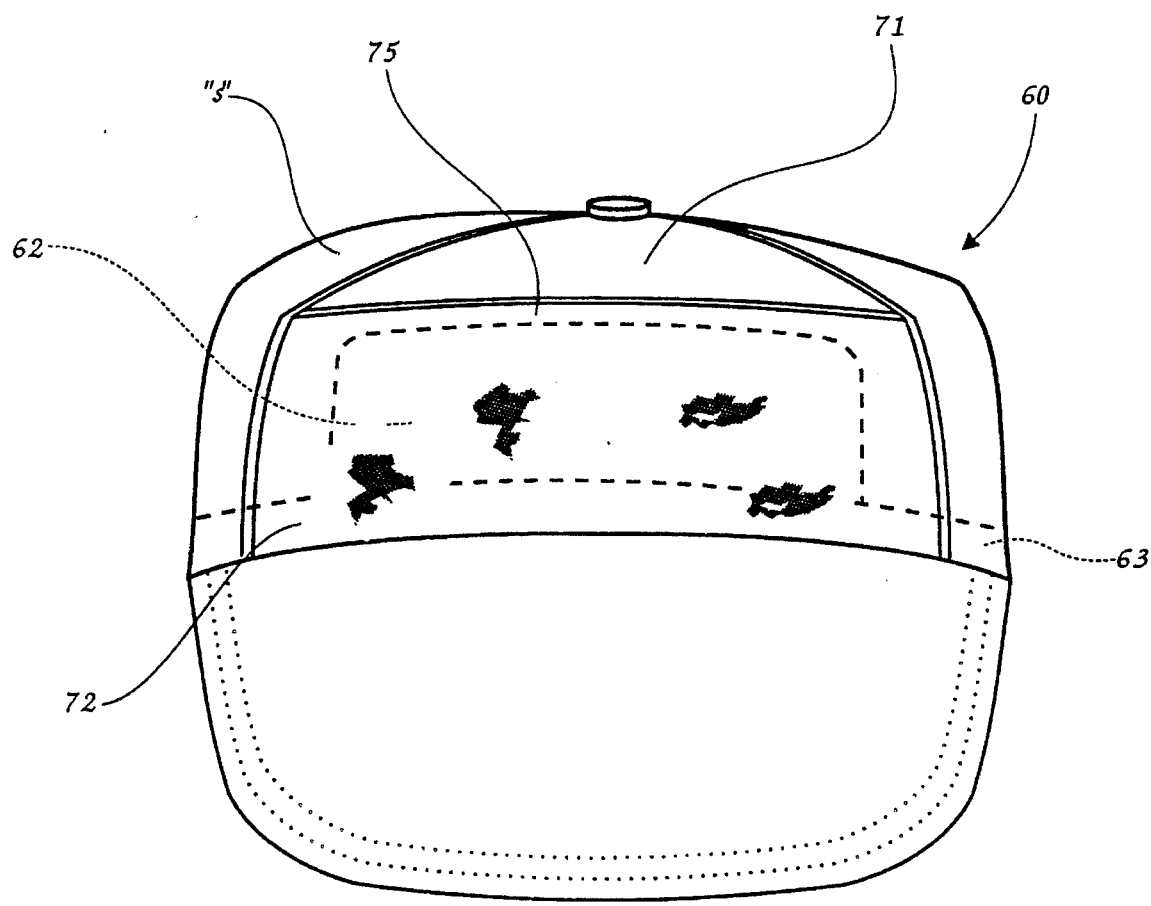
FIG. 13 is a front view of the hat illustrated in FIG. 12.

As shown in FIGS. 12 and 13, the outer shell fabric "S" of a moisture management hat 60 may include one or more moisture evaporation panels 71 and 72 in combination with a moisture transport insert 62 and moisture management band 63, as described above. A first moisture evaporation panel 71 is preferably located in a front crown portion 75 of the hat 60, adjacent to the shell-side surface of the moisture transport insert 62. Additionally, a second moisture evaporation panel 72 may be located adjacent to the shell-side surface of the moisture management band 63.

The moisture evaporation panels 71 and 72 are preferably constructed of an air permeable, relatively open knit or woven mesh fabric. The mesh fabric may include either hydrophobic or hydrophilic fibers. Preferably, the mesh fabric of the evaporation panels 71 and 72 includes moisture wicking fibers, such as hydrophilic nylon fibers which have been chemically treated by a process developed by the Intera Corporation to enhance the fibers' ability to quickly wick and disperse moisture.

According to one preferred embodiment, the mesh fabric has approximately 120 openings per square inch (20 openings per square centimeter). The panels 71 and 72 are designed to be especially permeable to air in order to facilitate the evaporation of moisture from the moisture transport insert 62 and the moisture management band 63. The moisture evaporation panels 71 and 72 comprise the outermost exterior component of the moisture management hat 60, and are attached along respective edges to the remaining shell fabric "S" of the moisture management hat 60.

Each of the various components of the invention may be attached together by any conventional garment construction technique. Additionally, the respective components may be attached to the moisture management hat 10, 20, 40, 50, and 60 by convention garment construction techniques, particularly overedge sewing stitches. For example, the moisture transport insert 13 and moisture management band 12 of the moisture management hat 10 may be attached to the inside surface of the moisture management hat 10 by sewing the respective edges of these components to the hat 10.

In an alternate embodiment (not shown), the moisture transport insert may be attached to a relatively stiff, open mesh panel having a shape corresponding generally to the shape of the moisture transport insert. Preferably, the relatively stiff panel is constructed of a nylon or polyester mesh fabric which may be knit or woven. The base or bottom edge of the panel is attached to the inside perimeter of the hat, just above the moisture management band. The unattached body portion of the panel extends upwardly into the hat, adjacent to the inside crown portion of the hat. The moisture transport insert is supported by the relatively stiff panel.

A moisture management hat is described above. Various details of the invention may be changed without departing from its scope. Furthermore, the foregoing description of the preferred embodiment of the invention and the best mode for practicing the invention are provided for the purpose of illustration only and not for the purpose of limitation-the invention being defined by the claims.

I claim:

1. A moisture management hat constructed of a shell fabric, the shell fabric including a moisture evaporation panel located on a front crown portion of said hat, said evaporation panel being constructed of an air permeable, relatively open knit or woven fabric, and said moisture management hat comprising a moisture management band located along an inside perimeter of the hat for residing next to at least the forehead of the wearer during garment wear, said moisture management band comprising:

(a) a first, moisture wicking fabric layer having a skin-side surface and a shell-side surface, said first fabric layer constructed of hydrophobic fibers for residing nearest the head of the wearer for moving moisture outwardly away from the head; and (b) a second, moisture dispersal fabric layer having a skin-side surface and a shell-side surface, said second fabric layer residing adjacent to the shell-side surface of said first fabric layer and constructed of hydrophilic fibers for receiving and dispersing moisture wicked outwardly by said first fabric layer.

2. A moisture management hat according to claim 1, wherein the skin side surface of said first fabric layer is brushed to raise the hydrophobic fibers and enhance the outward movement of moisture along the fibers.

3. A moisture management hat according to claim 1, further comprising a third fabric layer having a skin-side surface and a shell-side surface, said third fabric layer being integrally knit with said first and second fabric layers and residing substantially adjacent to the shell-side surface of said second fabric layer; said third fabric layer constructed of hydrophilic fibers for further receiving and dispersing moisture moved outwardly by said first and second fabric layers.

4. A moisture management hat according to claim 3, wherein the shell-side surface of said third fabric layer is brushed to increase the quantity of hydrophilic fiber ends extending from said moisture management band, thereby increasing the fabric surface area available for air exposure and enhancing the evaporation of moisture from said moisture management band.

5. A moisture management hat constructed of a shell fabric, said hat comprising:

(a) a moisture management band located along an inside perimeter of said hat for residing next to at least the forehead of the wearer during garment wear, said moisture management band comprising:

(1) a first, moisture wicking fabric layer having a skin-side surface and a shell-side surface, said first fabric layer constructed of hydrophobic fibers for moving moisture outwardly away from the head of the wearer;

(2) a second, moisture dispersal fabric layer having a skin-side surface and a shell-side surface, said second fabric layer residing adjacent to the shell-side surface of said first fabric layer, and constructed of hydrophilic fibers for receiving and dispersing moisture wicked outwardly by said first fabric layer; and (b) a moisture transport insert located generally at an inside front crown portion of said hat and having a lower section residing adjacent to the shell-side surface of the second fabric layer of the moisture management band, said moisture transport insert comprising a first fabric layer having a skin-side surface and a shell-side surface, said first fabric layer constructed of hydrophobic wicking fibers for moving moisture outwardly and upwardly away from the forehead of the wearer.

6. A moisture management hat according to claim 5, wherein said moisture transport insert further comprises a second fabric layer having a skin-side surface and a shell-side surface, said second fabric layer being integrally knit with said first fabric layer of said moisture transport insert and residing adjacent to the shell-side surface of said first fabric layer; said second fabric layer constructed of hydrophilic fibers for moving moisture outwardly away from the forehead and upwardly towards the front crown portion of the hat for dispersal and evaporation.

7. A moisture management hat according to claim 6 wherein said moisture transport insert further comprises a third fabric layer having a skin-side surface and a shell-side surface, said third fabric layer being integrally knit with said first and second fabric layers of said moisture transport insert and residing adjacent to the shell-side surface of said second fabric layer; said third fabric layer constructed of hydrophilic fibers for moving moisture outwardly away from the forehead and upwardly towards the front crown portion of the hat for dispersal and evaporation.

8. A moisture management hat according to claim 7, wherein the shell-side surface of said third fabric layer is brushed to increase the quantity of hydrophilic fiber ends extending from said moisture transport insert, thereby increasing the fabric surface area available for air exposure and enhancing the evaporation of moisture from said moisture transport insert.

9. A moisture management hat according to claim 5, wherein the shell fabric of said hat comprises a first moisture evaporation panel located on a front crown portion of said hat, said first evaporation panel constructed of an air permeable, relatively open knit or woven fabric.

10. A moisture management hat according to claim 9, wherein the shell fabric of said hat further comprises a second moisture evaporation panel located along the perimeter of said hat generally adjacent to said moisture management band, said second moisture evaporation panel constructed of an air permeable, relatively open knit or woven fabric.

11. A moisture management hat constructed of a shell fabric and comprising a moisture management band located along an inside perimeter of the hat for residing next to at least the forehead of the wearer during garment wear, the shell fabric including a moisture evaporation panel constructed of an air permeable, relatively open knit or woven fabric located along the perimeter of said hat generally adjacent to said moisture management band, said moisture management band comprising:
- (a) a first, moisture wicking fabric layer having a skin-side surface and a shell-side surface, said first fabric layer being constructed of hydrophobic fibers for residing nearest the head of the wearer for moving moisture outwardly away from the head; and
- (b) a second, moisture dispersal fabric layer having a skin-side surface and a shell-side surface, said second fabric layer residing adjacent to the shell-side surface of said first fabric layer and constructed of hydrophilic fibers for receiving and dispersing moisture wicked outwardly by said first fabric layer.

12. A moisture management hat constructed of a shell fabric and comprising a moisture management band located along an inside perimeter of the hat for residing next to at least the forehead of the wearer during garment wear, said moisture management band comprising:
- (a) a first, moisture wicking fabric layer comprising hydrophobic fibers for residing nearest the head of the wearer for moving moisture outwardly away from the head; and
- (b) a second, moisture dispersal fabric layer integrally knit with said first fabric layer, and comprising hydrophilic fibers for receiving and dispersing moisture wicked outwardly by said first fabric layer.

* * * * *